US006517343B2

(12) United States Patent
Jones et al.

(10) Patent No.: US 6,517,343 B2
(45) Date of Patent: Feb. 11, 2003

(54) COATED CANDLES AND COATING COMPOSITIONS

(75) Inventors: Raymond H. Jones, Lynn Haven, FL (US); Charles D. Moses, Callaway, FL (US); Ronald L. Gordon, Springfield, GA (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

(21) Appl. No.: 09/874,380

(22) Filed: Jun. 4, 2001

(65) Prior Publication Data

US 2002/0013444 A1 Jan. 31, 2002

Related U.S. Application Data

(63) Continuation-in-part of application No. 09/292,486, filed on Apr. 15, 1999, now Pat. No. 6,242,509, which is a continuation of application No. PCT/US97/18821, filed on Oct. 18, 1997, and a continuation-in-part of application No. 08/939,034, filed on Sep. 26, 1997, now Pat. No. 6,111,055.

(51) Int. Cl.[7] .............. F23D 3/16; C08G 69/08
(52) U.S. Cl. ............. 431/288; 431/289; 431/291; 528/170; 528/295.5; 528/296; 528/310; 528/322; 528/332; 528/339; 528/339.5; 528/343; 528/345; 44/265; 44/235; 44/459; 522/164; 522/175; 427/447; 427/487; 427/496
(58) Field of Search ............... 528/170, 295.5, 528/296, 310, 322, 332, 339, 339.5, 343, 345; 427/447, 487, 496; 431/288, 289, 291; 44/265, 275, 459; 522/164, 175

(56) References Cited

U.S. PATENT DOCUMENTS

| | | | |
|---|---|---|---|
| 2,279,137 A | 4/1942 | Guilfoil, Jr. ............ 67/21 |
| 2,379,413 A | 7/1945 | Bradley ............... 260/404.5 |
| 2,450,940 A | 10/1948 | Cowan et al. ......... 260/404.5 |
| 2,662,068 A | 12/1953 | Floyd ................. 260/33.6 |
| 2,861,048 A | 11/1958 | Wright et al. ........... 260/22 |
| 3,141,787 A | 7/1964 | Goetze et al. .......... 106/252 |
| 3,148,125 A | 9/1964 | Strianse et al. ......... 167/85 |
| 3,156,572 A | 11/1964 | Carlick et al. ........... 106/27 |
| 3,341,465 A | 9/1967 | Kaufman et al. ......... 252/316 |
| 3,420,789 A | 1/1969 | Wilson ................. 260/18 |
| 3,595,816 A | 7/1971 | Barrett ................. 260/18 |
| 3,615,289 A | 10/1971 | Felton ................. 44/7.5 |
| 3,645,705 A | 2/1972 | Miller et al. ............ 44/7.5 |
| 3,741,711 A | 6/1973 | Bryant ................. 431/125 |
| 3,819,342 A | 6/1974 | Gunderman et al. ....... 44/7.5 |
| 3,844,916 A | 10/1974 | Gaske ................. 204/159.16 |
| 3,925,349 A | 12/1975 | Gaske ................. 204/159.15 |
| 4,045,416 A | 8/1977 | Robson et al. ........... 260/77.5 |
| 4,051,159 A | 9/1977 | Tsoucalas et al. ....... 260/404.5 |
| 4,062,819 A | 12/1977 | Mains et al. ............ 260/18 N |
| 4,075,366 A | 2/1978 | Packer et al. ............ 427/44 |
| 4,115,370 A | 9/1978 | Corrado ............... 260/22 CQ |
| 4,116,787 A | 9/1978 | Gatechair ............. 204/159.23 |
| 4,128,436 A | 12/1978 | O'Hara et al. ........... 106/243 |
| 4,147,253 A | 4/1979 | Brook et al. ........... 206/205 |
| 4,150,002 A | 4/1979 | Drawert et al. ......... 260/18 N |
| 4,198,331 A | 4/1980 | Buchwalter et al. ..... 260/29.2 EP |
| 4,248,753 A | 2/1981 | Buchwalter et al. ..... 260/29.2 TN |
| 4,252,734 A | 2/1981 | Barry et al. ........... 260/404.5 |
| 4,256,560 A | 3/1981 | Buchwalter et al. ..... 204/181 C |
| 4,259,183 A | 3/1981 | Cadotte ............... 210/654 |
| 4,275,054 A | 6/1981 | Sebag et al. ............ 424/65 |
| 4,284,776 A | 8/1981 | Gruber et al. ......... 544/400 |

(List continued on next page.)

FOREIGN PATENT DOCUMENTS

| | | |
|---|---|---|
| EP | 469 435 B1 | 1/1995 |
| EP | 467 533 B1 | 11/1997 |
| JP | 08-92369 | 4/1996 |
| WO | WO 88/00603 | 1/1988 |
| WO | WO 93/21240 | 10/1993 |
| WO | WO 97/08282 | 3/1997 |
| WO | WO 98/17243 | 4/1998 |
| WO | WO 98/17705 | 4/1998 |
| WO | WO 00/40216 | 7/2000 |
| WO | WO 00/46326 | 8/2000 |

OTHER PUBLICATIONS

Solutia, Data Sheet:Modaflow 2100 Resin, Publication No. 2118127C, Sep. 26, 2000.

Tóth et al., "Analytical Performances of Lipophilic Diamides Based Alkaline Earth Ion–Selective Electrodes," *Electoanalysis* 5 (9–10):781–790, 1993, The month is not available in the date of publication.

Vedanayagam et al., "Kinetics of Reaction of C36 Dimeric Fatty Acids and Ethylenediamine in Solution," *J. of Applied Polymer Science* 45(12):2245–2248, Aug. 25, 1992.

Yasuda et al., "Novel Low–Molecular–Weight Organic Gels: N,N', N'–Tristearyltrimesamide/Organic Solvent System," *Chemistry Letters*, pp. 575–576, 1996, The Month is Not Available in the Date of Publication.

Abstract of JP05–156220, Accession No. 1993–232596, Jun. 22, 1993.

Primary Examiner—P. Hampton-Hightower
(74) Attorney, Agent, or Firm—Seed Intellectual Property Law Group PLLC

(57) ABSTRACT

A curable composition is placed on a candle, and then the composition is exposed to curing conditions such as ultraviolet light, to thereby cure the coating composition and provide a candle having a cured coating. The curable composition may be the reaction product of TMPTA (trimethylolpropanetriacrylate), itself the reaction product of trimethylolpropane and acrylic acid) and oleyl amine (an unsaturated primary amine having eighteen carbons). The candle may be made of wax or a gelled solvent, i.e., a mixture of gellant and solvent, particularly a hydrocarbon or other low polarity solvent. The undiluted coating may be applied by spraying on the oily surface of the candle. Ultraviolet cure of the coating occurs in 1–2 seconds.

29 Claims, No Drawings

U.S. PATENT DOCUMENTS

| | | | | |
|---|---|---|---|---|
| 4,330,640 | A | 5/1982 | Buchwalter | 524/555 |
| 4,337,298 | A | 6/1982 | Karim et al. | 428/461 |
| 4,341,671 | A | 7/1982 | Bolze et al. | 528/324 |
| 4,346,024 | A | 8/1982 | Coquard et al. | 524/219 |
| 4,369,232 | A | 1/1983 | Scopazzi | 428/425.9 |
| 4,369,284 | A | 1/1983 | Chen | 524/476 |
| 4,376,194 | A | 3/1983 | Tanaka et al. | 528/288 |
| 4,427,366 | A | 1/1984 | Moore | 431/291 |
| 4,438,240 | A | 3/1984 | Tanaka et al. | 525/420 |
| 4,449,987 | A | 5/1984 | Lindauer | 44/7.5 |
| 4,504,630 | A | 3/1985 | Buchwalter | 525/296 |
| 4,552,693 | A | 11/1985 | Hussain et al. | 252/522 A |
| 4,568,270 | A | 2/1986 | Marcus et al. | 431/288 |
| 4,571,267 | A | 2/1986 | Drawert et al. | 106/27 |
| 4,663,428 | A | 5/1987 | Okitu et al. | 528/324 |
| 4,742,128 | A | 5/1988 | Frisch et al. | 525/424 |
| 4,742,147 | A | 5/1988 | Nichols | 528/75 |
| 4,760,117 | A | 7/1988 | Evans et al. | 525/394 |
| 4,769,285 | A | 9/1988 | Rasmussen | 428/355 |
| 4,816,549 | A | 3/1989 | Rumack | 528/336 |
| 4,826,428 | A | 5/1989 | Lam | 431/291 |
| 4,855,098 | A | 8/1989 | Taylor | 264/103 |
| 4,937,069 | A | 6/1990 | Shin | 424/66 |
| 4,937,701 | A | 6/1990 | Schroder | 362/161 |
| 4,946,922 | A | 8/1990 | Reisch et al. | 528/76 |
| 5,069,897 | A | 12/1991 | Orr | 424/66 |
| 5,084,536 | A | 1/1992 | Brindöpke et al. | 526/218.1 |
| 5,102,656 | A | 4/1992 | Kasat | 424/66 |
| 5,132,355 | A | 7/1992 | Nahlovsky | 524/474 |
| 5,177,177 | A | 1/1993 | Thullen et al. | 528/339.3 |
| 5,180,424 | A | 1/1993 | Hutter | 106/20 R |
| 5,180,802 | A | 1/1993 | Hartman et al. | 528/335 |
| 5,221,534 | A | 6/1993 | DesLauriers et al. | 424/78.03 |
| 5,338,187 | A | 8/1994 | Elharar | 431/288 |
| 5,342,894 | A | 8/1994 | Robeson et al. | 525/183 |
| 5,364,924 | A | 11/1994 | Gerkin et al. | 528/73 |
| 5,372,852 | A | 12/1994 | Titterington et al. | 427/288 |
| 5,395,233 | A | 3/1995 | Karp | 431/289 |
| 5,432,204 | A | 7/1995 | Farkas | 521/49 |
| 5,482,649 | A | 1/1996 | Meixner et al. | 252/182.18 |
| 5,500,209 | A | 3/1996 | Ross et al. | 424/66 |
| 5,527,368 | A | 6/1996 | Supkis et al. | 51/298 |
| 5,538,718 | A | 7/1996 | Aul et al. | 424/64 |
| 5,565,246 | A | 10/1996 | Hyde | 427/504 |
| 5,578,089 | A | 11/1996 | Elsamaloty | 44/275 |
| 5,597,300 | A | 1/1997 | Wohl et al. | 431/288 |
| 5,603,925 | A | 2/1997 | Ross et al. | 424/65 |
| 5,632,615 | A | 5/1997 | DeGarmo | 431/288 |
| 5,645,632 | A | 7/1997 | Pavlin | 106/31.29 |
| 5,693,277 | A | 12/1997 | Widmer | 264/153 |
| 5,728,750 | A | 3/1998 | Schwalm et al. | 522/173 |
| 5,783,657 | A | 7/1998 | Pavlin et al. | 528/310 |
| 5,859,084 | A | 1/1999 | Schröder et al. | 522/34 |
| D411,891 | S | 7/1999 | Bell et al. | D26/6 |
| 6,068,472 | A | 5/2000 | Freeman et al. | 431/291 |
| 6,111,055 | A | 8/2000 | Berger et al. | 528/310 |
| 6,129,771 | A | 10/2000 | Ficke et al. | 44/275 |
| 6,172,129 | B1 | 1/2001 | Fan et al. | 522/167 |
| 6,214,063 | B1 | 4/2001 | DeStefano et al. | 44/275 |
| 6,214,290 | B1 | 4/2001 | Esposito | 422/1 |
| 2002/0013444 | A1 | 1/2002 | Jones et al. | 528/170 |

COATED CANDLES AND COATING COMPOSITIONS

CROSS-REFERENCES TO RELATED APPLICATIONS

This application is a continuation-in-part of U.S. patent application Ser. No. 09/292,486 filed Apr. 15, 1999, now U.S. Pat. No. 6,242,509, which is both a continuation of PCT/US97/18821 having an International Filing Date of Oct. 18, 1997, and a continuation-in-part of U.S. patent application Ser. No. 08/939,034, filed Sep. 26, 1997, now U.S. Pat. No. 6,111,055 issued Aug. 29, 2000, where this application fully incorporates by reference each of the above-listed patents and applications.

TECHNICAL FIELD

The invention relates to candles and in particular to candles having a cured coating, and methods for their preparation.

BACKGROUND OF THE INVENTION

Candlemaking is an ancient art that continues to see improvements, driven largely by the basic aesthetic appeal of candles to the general public. A very common type of candle consists of a wick embedded in a block of paraffin wax, where the wax provides the fuel for the burning candle. Paraffin is an inexpensive raw material, which makes it an economically attractive ingredient for a candle. Paraffin is a convenient material to mold into various shapes, and accepts coloration so a wide variety of colorful and variously shaped candles can be made from paraffin. A fundamental property of paraffin is its opaqueness. Opaqueness is disadvantageous in that any visually interesting objects placed within a paraffin candle are essentially invisible, unless those objects are placed very near the surface of the candle. Also, while paraffin is generally considered comfortable to touch, it can undesirably rub off onto skin.

A modern variation on candlemaking is the use of gelled fuel in place of paraffin. Some gelled fuels have the advantage of being clear or transparent so that decorative items that are placed within a transparent candle are visible to the consumer. This transparency adds an extra dimension to candlemaking and candle design, in that it allows the creation of many interesting and commercially desirable candles. Typically, a gelled fuel is made by combining a gellant and a solvent that is gelled by the gellant. In some instances, the gelled fuel will display undesirable syneresis, which refers to a physical separation of the gellant from the fuel. Syneresis causes a gelled fuel to have a very oily feel, which is typically undesirable. Even in the absence of syneresis, a gelled fuel tends, to a greater extent than a paraffin candle, to pick up fingerprints and so does not maintain a transparent surface.

Accordingly, there is a need in the art for transparent candles that do not feel oily to the touch, do not create fingerprints when handled, and if syneresis does occur, the syneresis does not impact the feel of the candle. As disclosed herein, the present invention is directed to fulfilling this and related needs.

SUMMARY OF THE INVENTION

The present invention provides a curable composition that is placed on a candle, and then the composition is exposed to curing conditions such as ultraviolet light, to thereby cure the coating composition and provide a candle having a cured coating. The curable composition may be the reaction product of TMPTA (trimethylolpropane-triacrylate), itself the reaction product of trimethylolpropane and acrylic acid) and oleyl amine (an unsaturated primary amine having eighteen carbons). The candle may be made of wax or a gelled solvent, i.e., a mixture of gellant and solvent, particularly a hydrocarbon or other low polarity solvent. The undiluted coating may be applied by spraying on the oily surface of the candle. Ultraviolet cure of the coating occurs in 1–2 seconds.

Thus, in one aspect the invention provides a candle, where the candle includes a wick, a fuel, and a cured coating. The fuel may be or include a gellant, such as ETPA or ATPA gellant, in addition to a solvent that it gelled by the gellant, such as mineral oil or a fatty acid triglyceride. The fuel may also be or include wax. The candle may contain more than one visible phase, for example, the candle may include one or more icons set within the fuel.

The coating may be a UV-cured coating. A preferred UV-cured coating includes a reaction product of a tri(meth)acrylate, i.e., a triacrylate or a trimethyacrylate or a mixture of three of acrylate and methacrylate, and a primary amine. The tri(meth)acrylate may be the esterification product of a triol and acrylic acid, and the primary amine may be a primary $C_{14}$–$C_{22}$ fatty amine. An exemplary esterification product of a triol and acrylic acid is trimethylolpropane triacrylate, and an exemplary primary $C_{14}$–$C_{22}$ fatty amine is oleyl amine. The coating also preferably includes a leveling agent, which when present provides a smoother coating with better adhesion to the candle. The coating also needs to contain a photoinitiator when the coating is to be cured by UV-radiation. The coating may, but need not also include one or more additives selected from colorant, fragrance, flame retardant and insect repellant.

Thus, the present invention provides a candle that includes a wick, a fuel, and a cured coating, where the cured coating is the reaction product of UV-curing a coating composition. The coating composition includes a reaction product of a primary $C_{14}$–$C_{22}$ fatty amine with a poly(meth)acrylate, a leveling agent and a photoinitiator. In preferred embodiments, the primary amine is oleyl amine and the poly(meth)acrylate is trimethylolpropane triacrylate.

In another aspect, the present invention provides a method for coating a candle using a curable composition. The method includes (a) reacting a primary amine with a triacrylate to form a product; (b) applying the product to a surface of a candle to provide a curable coating on said candle; and (c) curing the curable coating with radiation, to provide a cured coating on said candle. The product may be applied by, e.g., spraying, brushing, dipping, or sponging, where spraying is a preferred method. The coating composition may be applied more than once, to provide a multiply coated candle. The multiple coatings may look the same or different. When the curable coating is cured by UV radiation, the product further should include a photosensitizer or a photoinitiator. In addition, to assist in wetting the surface of the hydrophobic surface present in the candle, the product may further include a leveling agent or a flow modifier. A suitable flow modified is a copolymer of ethyl acrylate and 2-ethylhexyl acrylate, where the copolymer has a viscosity at 25° C. of 5,000 to 12,000 centipoise. The primary amine is preferably a $C_{14}$–$C_{22}$ primary amine, where the fatty nature of this type of primary amine enhances the ability of the curable composition to adhere to the hydrophobic surface of the candle. Oleyl amine is a suitable fatty primary amine. Trimethylolpropane triacrylate is a suitable triacrylate.

Thus, the present invention provides a method for coating a candle using a curable composition, where the method includes (a) reacting a $C_{14}$–$C_{22}$ primary fatty amine with a triacrylate to form a product, the product further comprising a photoinitiator and a leveling agent; (b) applying the product to a surface of a candle to provide a UV-curable coating on said candle; and (c) curing the curable coating with UV radiation, to provide a cured coating on said candle. In one aspect of the invention, the leveling agent is a copolymer of ethyl acrylate and 2-ethylhexyl acrylate, said copolymer having a viscosity at 25° C. of 5,000 to 12,000 centipoise.

In another aspect, the present invention provides a radiation curable composition that includes a reaction product of a primary $C_{14}$–$C_{22}$ fatty amine with a poly(meth)acrylate. In preferred embodiments, the amine is oleyl amine and/or the poly(meth)acrylate is trimethylolpropane triacrylate. In one embodiment, the composition also includes a leveling agent, such as a copolymer of ethyl acrylate and 2-ethylhexyl acrylate, where the copolymer has a viscosity at 25° C. of 5,000 to 12,000 centipoise, and in one aspect has a viscosity of 20–5000 cps at 25° C. The composition may also include a diluent, and should, prior to exposure to UV radiation, also include a photoinitiator in an amount effective to initiate the UV cure.

Thus, the present invention provides a UV-curable composition that includes a reaction product of a primary $C_{14}$–$C_{22}$ fatty amine with a poly(meth)acrylate, wherein the primary amine is oleyl amine, the poly(meth)acrylate is trimethylolpropane triacrylate, and where the composition further includes a leveling agent and a photoinitiator. The leveling agent may be a copolymer of ethyl acrylate and 2-ethylhexyl acrylate, where the copolymer has a viscosity at 25° C. of 5,000 to 12,000 centipoise, and the composition has a viscosity of 20–5000 cps at 25° C.

DETAILED DESCRIPTION OF THE INVENTION

The present invention provides a candle that includes a wick, a fuel, and a cured coating. The cured coating affords the candle with many desirable properties. As mentioned above, some candle fuels, and particularly candles prepared from gelled fuel, will tend to pick up fingerprints when handled. The present invention solves this problem by providing a cured coating that is positioned on the outside of the candle. The cured coating typically has a non-oily feel, and in fact typically feels dry to the touch without readily receiving fingerprints. Thus the invention provides for a candle that may be repeatedly handled by a consumer without leaving telltale fingerprints, so long as the candle fuel contains a coating.

The prepolymer coating composition is particularly suitable for application onto hydrophobic or oily surfaces, such as those surfaces found on wax and gel candles. Since the coating can have a transparent appearance, it is particularly desirable for transparent candles. Furthermore, the coating typically imparts some mechanical strength to the article, which would not be present in its absence. Some candle fuels are somewhat soft, and candles made from these soft fuels may benefit from the increased mechanical strength afforded by the cured coating during, for example, shipping and storage of the article.

The coating may also enhance the clarity of the candle by imparting a rigid yet very smooth surface to the candle body. The coating may be made to be extremely smooth and to have a highly polished appearance. Even when the underlying candle fuel itself is transparent, the surface of the candle fuel may not be completely smooth, in part due to a degree of softness that is typically present in gelled candle fuels. However, when a hard transparent coating is placed on the surface of a candle fuel, then a very smooth and flawless exterior surface can be achieved. This smooth surface imparts a greater appearance of clarity to the candle fuel. The transparent coating may also improve the refractive index of the exterior of the candle fuel.

The coating of the present invention, when placed on a candle, is preferably clear and colorless or essentially colorless. In addition, the coating is solid, preferably not brittle, and yet not so soft that it is easily deformed after application to the candle fuel. The coating may contain optional ingredients, such as colorant, fragrance, flame retardant, insect-repellant, and the like.

In one aspect, the invention provides a radiation curable composition that provides a radiation cured coating. In a preferred embodiment, the radiation curable composition is cured upon exposure to ultraviolet light, i.e., is a UV-curable coating. According to the present invention, it has been recognized that a particularly effective composition for preparing an UV-cured coating is the reaction product of a triacrylate and a primary amine. This general type of reaction, where an amine is reacted with an alpha-beta-unsaturated carbonyl moiety, is commonly referred to in the art as a Michael addition or a Michael reaction. In one aspect of the invention the Michael addition involves a primary amine adducting with a stoichiometric excess of ethylenic material such as a polyacrylate to form an adduct containing unreacted acrylate groups and at least one tertiary beta amino group. The Michael addition reaction product is referred to herein as a prepolymer.

Many prepolymers formed between amines and polyacrylates are known in the art, and may be used to form a coating on a candle according to the present invention. While the prior art has recognized that certain Michael reaction products can be cured by exposure to UV radiation, it has not previously been recognized that these prepolymers are particularly good at providing a coating on a hydrophobic or oily surface, as is found in a candle.

In one aspect, the prepolymer composition of the invention is formed by reacting a primary $C_{14}$–$C_{22}$ fatty amine with a polyacrylate or polymethacrylate. The polyacrylate is readily formed by reaction between a polyol, also known as a polyhydric compound, which is an organic chemical having a plurality of hydroxyl groups, and acrylic or methacrylic acid or an ester thereof. The hydroxyl groups react with the acid/ester groups of the acrylic/methacrylic or acrylate/methacrylate compound to form an ester leaving reactive olefinic groups. These olefinic groups are available to react with primary or other amines to form a Michael addition product.

The primary amine is preferably a hydrocarbon group substituted with an amino group, i.e., a compound of the formula $R^1$—$NH_2$ wherein $R^1$ is a hydrocarbon group. The hydrocarbon group is preferably "fatty" in that it contains at least about 14 carbon atoms, and up to about 22 carbon atoms. When the hydrocarbon group is fatty, it has good comparability with the oily or waxy surface of a candle, and this compatability is advantageous in forming a coating on a candle made from gelled fuel or wax.

A preferred primary $C_{14}$–$C_{22}$ fatty amine is oleyl amine. Oleyl amine may be reacted with a polyacrylate or polymethacrylate to form a prepolymer composition suitable for hydrophobic or oily surfaces. In still another aspect of the invention, a preferred polyacrylate is trimethylolpropane triacrylate (also known as TMPTA). Trimethylolpropane triacrylate may be reacted with a primary amine to form a prepolymer composition suitable for hydrophobic or oily surfaces.

The prepolymer composition may include a leveling agent. Leveling agents are well known in the art, and are used most often to enhance the consistency of prepolymer textures. Leveling agents are also commonly referred to in the art as flow modifiers. Leveling agents/flow modifiers reduce or eliminate beading and streaking of coating compositions both before and during the cure process. In a preferred embodiment of the invention, the prepolymer composition includes a leveling agent. Leveling agents are available from various sources: MODAFLOW® 2100 Resin (Solutia Inc., St. Louis, Mo.), LANCO™ FLOW U (www.lubrizol.com), and PERENOL® F-60 (www.fitzchem.com) are just a few. The leveling agent known as MODAFLOW® 2100 Resin is a clear, colorless to pale yellow liquid, having the chemical composition of an ethyl acrylate, 2-ethylhexyl acrylate copolymer, assigned Chemical Abstracts Registry No. 26376-86-3, an AHPA color of 0–80, preferably about 30, and a viscosity (Brookfield, 25C) of 5,000 to 12,000 cps, preferably about 6,800. Flurochemical surfactants may also be used as the flow modifier. Silicon-based flow modifiers are not preferred as they can be incompatible with the prepolymer.

The prepolymer composition preferably exhibits a viscosity suitable for application by a coating process. The viscosity of a material is a property relating to a fluid's resistance to sheering forces. The lower the viscosity of a material, the more free-flowing the material is. Viscosity may decrease as temperature increases. Suitable compositions for coatings may require lower viscosity depending upon the particular application technique. For example, it is desirable for a composition to have a low viscosity when a material is applied by spraying. Those skilled in the art will appreciate that when a material is applied by brushing, the viscosity need not be as low as the viscosity of a material that is applied by spraying.

A viscosity of about 20–5000, preferably 100–4000 centipoise (cps) at 25° C. is desirable for a prepolymer composition of the present invention. At this viscosity, the prepolymer composition is readily applied to the surface of a candle by, e.g., spraying or dipping. Viscosity is commonly measured by many different methods, including the use of a Model LVTD Digital Viscometer from Brookfield Engineering Laboratories, Inc.

The prepolymer composition may also comprise a diluent. Diluents are well known in the art of UV curable coatings, and function to reduce the concentration of prepolymer, also referred to as "thinning" the fluid. Some diluents useful in UV curable compositions are listed in U.S. Pat. No. 4,207,155. The diluent may be reactive, in that it will not only reduce the viscosity of the prepolymer composition but it will also react under curing conditions so as to become a permanent part of the coating. Examples of reactive diluents are included in U.S. Pat. No. 6,169,126. Examples of non-reactive diluents include dioctyl phthalate, dibutyl phthalate, dioctyl adipate, petroleum solvents, etc. Diluents used with the present invention may be inert, non-reactive, volatile, or may copolymerize during curing and/or diffuse into the candle fuel.

The candles of the present invention include a wick. A wick is a material that conveys liquid by capillary action. A common type of wick that may be used in the present invention is a cord or strand of loosely woven, twisted, or braided cotton fibers, that serves to draw up fuel to the flame by capillary action. Candles may possess one wick or a plurality of wicks. The candle preferably contains a single wick, where the wick is preferably positioned in the center of the candle.

A preferred wick is made from uniform, tear-resistant cotton yarn made of medium- and long-stapled cotton which is seasoned and does not have moisture damage. A typical wick has from 15–42 strands (plys). A larger wick (more strands) is preferred for a larger candle. A transparent wick may be used, so that an entire candle (wick plus fuel, and coating) may be transparent. Wicks may be obtained from a variety of commercial sources including CRAFTEX-PRESS™ (Memphis, Tenn. www.candlefactoryco.com), Atkins & Pearce, Inc. (Covington, Ky. www.braid.com) and www.candleandbathsupplies.com (Clarion, Iowa.).

The wick may be embedded with wax or other additive which facilitates or provides desired burning properties. For example, the wick may be colored using a water or alcohol soluble dye. Examples of water and alcohol soluble dyes that may be used to color the wick include, without limitation, F,D&C Blue #1, D&C Orange #4, Ext D&C Violet #2, F,D&C Red #4, D&C Red #33, F,D&C Red #40, D&C Green #8, D&C Yellow #10, F,D&C Yellow #5 and D&C Green #5.

In addition to the wick, the candle contains a fuel. In a typical candle, the fuel constitutes the primary component of the candle. A variety of candle fuels are known in the art and may be used in the present invention. Two common examples are gels and waxes. A precise definition of "gel" is not easy to give, although most if not all researchers recognize a "gel." Generally, a gel is more viscous than a liquid or paste, and retains its shape when left undisturbed, i.e., is self-supporting. However, a gel is typically not as hard or firm as a wax. Gels may be penetrated more easily than a wax-like solid, where "hard" gels are relatively more resistant to penetration than "soft" gels. A rigid gel as defined herein resists deformation upon the application of a force.

Almdale et al. (Polymer Gels and Networks, Vol. 1, No. 5 (1993)) list two criteria for defining a system as a gel: (1) a gel consists of two or more components, one of which is a liquid, present in substantial quantities; and (2) a gel is a soft material which is solid or solid-like. The solvents described herein include the liquid of Almdale. Whether Almdale's "soft material" is a gel can be described more accurately through rheological measurement. Typically, gels possess a storage modulus G'(w) which exhibits a pronounced plateau at higher frequencies (on the order of 1–100 radians/second), and a loss modulus G"(w) which is considerably smaller than the storage modulus in the plateau region. In a strict sense, the term "gel" applies to systems having a value G'(w) that is higher than its value of G"(w) at low frequencies. Many of the compositions according to the present invention are gels by one or both of the above definitions. A gel is free-standing or self-supporting in that its yield value is greater than the shear stress imposed by gravity.

In one aspect, the present invention provides a coating, and in particular a cured coating, for a candle wherein gelled solvent and gellant constitute the primary fuel. Suitable gellants are known in the art, and representative examples are described below.

A gel may be prepared by combining a polyamide resin (a gellant) with an oil (a solvent) as described in U.S. Pat. No.

3,645,705 to Miller et al. As set forth in Miller, the polyamide resin may be a long chain linear amide resin derived from the reaction of dimerized linoleic acid with di- or polyamines. The polyamide resin typically has a molecular weight (number or weight average) in the range of 6,000 to 9,000 and a softening point in the range of 48° C. to 185° C., and is capable of producing a gel structure in oil when the solubility of the polyamide in the oil is exceeded. The polyamide resin typically constitutes about 7–50% of the total weight of the gel. The oil may be a natural oil, such as castor oil, peanut oil, safflower oil, sunflower oil, corn oil or cod liver oil, having an iodine value in the range of 40 to 135. The oil may be a light, clear mineral oil. The article is readily formed by combining the various constituents at elevated temperature until a homogeneous mass is formed, and then cooling the mass to provide a gelled body.

Up to about 15% by weight of a methyl ester, such as methyl ricinoleate or methyl oleate, may be added to the composition to improve the stiffness and hardness of the article. An 8-, 10- or 12-carbon primary alcohol may be included within the composition that forms the gel, where the alcohol may serve to overcome a greasy or oily surface characteristic that the gel would otherwise have. The percentage of alcohol by weight should not be more than about 30% of the total material, the preferred range being 10–20%. As an article according to this aspect of the present invention has a coating on at least a portion of the surface of the gelled body, and this coating is intended, in part, to provide a pleasing, non-greasy surface to the gel, the incorporation of a primary alcohol in the formulation is not necessary.

Alternatively, the gel may be formed according to Gunderman et al., as set forth in U.S. Pat. No. 3,819,342. Thus, a thermoplastic polyamide resin and a solvent may be combined to form a gel. The polyamide resin is preferably formed by the reaction of an aliphatic polycarboxylic acid with a di- or polyamine. Most preferred are the reaction products of dimerized linoleic acid with di- or polyamines. These resins have an average molecular weight of between 2,000 and 10,000 and are described in great detail in U.S. Pat. Nos. 2,379,413 and 2,450,940.

The solvent of Gunderman et al. is capable of solubilizing the thermoplastic polyamide resin at a temperature below about 100° C., and is selected from the group consisting of unsaturated fatty acids, unsaturated fatty alcohols, saturated fatty alcohols, esters of fatty acids with polyhydric alcohols such as glycerol, and mixtures thereof. Specific suitable solvents include oleyl alcohol, linolenyl alcohol, palmitoleyl alcohol, linoleyl alcohol, mixtures thereof and the like. $C_6$–$C_{14}$ alcohols such as decanol dodecanol, hexanol, heptanol, octanol, nonanol and tetradecyl alcohol, and/or C10–C22 fatty acids such as ricinoleic, linoleic, oleic, linolenic, erucic, decylenic, dodecylenic and palmitoleic acids may be employed as the solvent. An ester such as castor oil, coconut oil derivatives, propylene glycol monolaurate, propylene glycol stearate, propylene glycol myristate and the like, may be used as well.

The polyamide and solvent of Gunderman et al. are combined in such a ratio that a gel results. For optimal performance, the article should contain from about 5 to 35 parts by weight of the thermoplastic polyamide resin. A preferred composition is one utilizing such a range of resin with an equivalent amount of oleyl alcohol. The article is readily formed by mixing the ingredients at elevated temperature to form a homogeneous composition, and allowing the composition to cool to a gel state.

Alternatively, the gel may be prepared according to U.S. Pat. No. 3,615,289 to Robert Felton. Thus, a gel may be formed by combining a solid polyamide resin, an alkanol amine or alkanol amide, and one or more stearic acid esters or a mixture of stearic acid esters and stearic acid. The composition comprises about 15 to 35 percent by weight polyamide resin, about 20 to 55 percent by weight of alkanol amine or alkanol amide, and about 1 to 50 percent by weight of stearic acid and esters thereof. The gels of Felton are readily formed by heating the components with stirring at a temperature of about 100–115° C. until the mixture is clear, and then allowing the mixture to cool to a gelled state.

The solid polyamide resin of Felton is the soluble condensation product of an aliphatic dicarboxylic acid and a diamine, the carboxyl and amino groups of adjacent monomer units being condensed to an amide linkage in the resin. The resin may also be based on carboxylic and amine compounds having more than two carboxyl and amino groups respectively. The resin is composed primarily of polyamides of molecular weight within the range of from about 2,000 to about 10,000, and are of the type generally set forth in U.S. Pat. No. 2,450,940. The alkanol amide may be prepared by the reaction of a fatty acid ester and an amine, wherein the ester and the amine are in substantially equal proportions. Among such compounds are the 1:1 and 2:1 (Kritchevsky type) diethanolamides of fatty acids, the 1:1 proportion being preferred. The preferred chain length for the fatty acid is about 14 to 24 carbon atoms. Suitable esters of stearic acid include isopropyl isostearate, butyl stearate, hexadecyl stearate, etc.

The gelled articles (candles) of Felton may contain a polyamide resin having at least some free carboxylic acid groups so that the polyamide resin has reactive character. This component may be present in a proportion of from about 5 to 10 percent by weight of the composition, and acts to prevent "sweating" by inhibiting the migration of the oil components. It also provides a smoother, glossier finish to the gelled body. This reactive polyamide may, but need not be present in the articles of the present invention, because the coating on articles of the present invention achieves the desired surface appearance and feel of the article, without reliance on the reactivity of the polyamide.

As a further alternative, the gel may be prepared by the procedures and reactants set forth in U.S. Pat. No. 5,578,089 to Mohamed Elsamaloty. According to Elsamaloty, a gel may be prepared from a hydrocarbon oil (a "solvent" of the present invention) and a blend of diblock and triblock copolymers based on synthetic thermal plastic rubbers. The hydrocarbon oil may be a cosmetic grade hydrocarbon oil (natural or synthetic) and is preferably a white oil. The oil may be a paraffinic oil, a naphthenic oil, natural mineral oil or the like. The rubber blend is prepared from at least one diblock and at least one triblock copolymer, in addition to one or more of radical copolymers and multiblock copolymers. Kraton® rubbers from Shell Chemical Company, which include styrene-butadiene-styrene copolymers and styrene-isoprene-styrene copolymers, are preferred. The gel is formed by blending the polymers and the oil, and then heating the blend to between about 50–90° C. to dissolve the polymers in the oil. Mixing may be carried out in any conventional manner. On cooling, a gel forms.

In one embodiment, the gel preferably consists of about 80–99 wt. % hydrocarbon oil and about 1–20, wt% of a blend of rubbers, where the rubbers are a blend of at least two different polymer members selected from the group consisting of diblock copolymers, triblock copolymers, radial block copolymers and multiblock copolymers, the gel including at least one diblock copolymer and at least one triblock copolymer, with the diblock and triblock polymers comprising segments of styrene monomer units and rubber monomer units. In another embodiment, the gel comprises from about 70% to about a 98% by weight of a hydrocarbon oil, from about 2% to about 30% by weight a copolymer selected from the group consisting of a triblock, radial block and multiblock copolymer, and from 0 to about 10% by weight of a diblock copolymer, as described in, e.g., International Publication No. WO 97/08282.

In a preferred aspect of the present invention, the gelled candle fuel includes ester terminated polyamide (ETPA) gellant as disclosed in U.S. Pat. No. 6,111,055 to Vivian Berger, et al. ETPA gels disclosed in that patent are prepared from one or more solvents mixed with ester terminated polyamide resins. In one aspect, the EPTA resin has the formula (1):

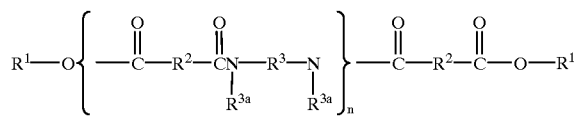

(1)

wherein n designates a number of repeating units such that ester groups constitute from 10% to 50% of the total of the ester and amide groups; $R^1$ at each occurrence is independently selected from an alkyl or alkenyl group containing at least 4 carbon atoms; $R^2$ at each occurrence is independently selected from a $C_{4-42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

In another aspect, the ETPA resin may be described as being prepared by reacting x equivalents of carboxylic acid from diacid or a reactive equivalent thereof, y equivalents of amine from diamine and z equivalents of hydroxyl from monoalcohol or a reactive equivalent thereof, wherein at least about 50% of the carboxylic acid equivalents are from polymerized fatty acid, monoalcohol is substantially the only monofunctional reactant used to form the resin, the monoalcohol has at least four carbon atoms, $0.9 \leq \{x/(y+z)\} \leq 1.1$, and $0.1 \leq \{z/(y+z)\} \leq 0.7$.

Suitable ETPA resins are commercially available from Arizona Chemical as their UNICLEAR™ resins.

In another preferred aspect of the present invention, the gelled candle fuel includes amide terminated polyamides (ATPA) gels as disclosed by Richard MacQueen et al. in PCT International Patent Application No. PCT/US00/00132, and also disclosed in U.S. patent application Ser. No. 09/25,889 filed Jan. 4, 1999, said application incorporated herein by reference. The ATPA gels disclosed by MacQueen et al. are formed by mixing a solvent with an ATPA resin. The ATPA resin may be represented by formula (1):

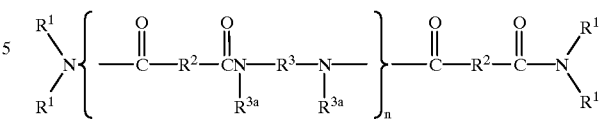

(1)

wherein, n designates a number of repeating units such that terminal amide groups constitute from 10% to 50% of the total amide groups; $R^1$ at each occurrence is independently selected from a $C_{1-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$.

The ATPA resin may also be described as being the reaction product obtained by reacting x equivalents of carboxylic acid from diacid or a reactive equivalent thereof, y equivalents of amine from diamine and z equivalents of a secondary amine-containing monoamine having no reactive functional groups except the secondary amine or a reactive equivalent thereof, where the monoamine is substantially the only monofunctional reactant used to form the resin, and wherein each of x, y and z is greater than 0. In a preferred embodiment, at least about 50% of the carboxylic acid equivalents are from polymerized fatty acid, $0.9 \leq \{x/(y+z)\} \leq 1.1$, and $0.1 \leq \{z/(y+z)\} \leq 0.7$, while in a further preferred embodiment, all equivalents of carboxylic acid come from polymerized fatty acid.

The candle fuel coated according to the present invention may contain a wax. Suitable waxes from which to prepare a candle include fully refined paraffin wax, or a partially refined (e.g., scale or slack) paraffin wax. The wax may be petroleum wax, including one or more of a paraffin, ceresine, ozokerite and microcrystalline wax. The wax may be a natural wax, such as candelilla wax, beeswax, or carnauba wax. The wax may be a synthetic wax, such as a product of the Fischer-Tropsch process, or a polyethylene wax. In a preferred embodiment, the first phase is a transparent gel and the second phase is a wax, where the wax has a melting point that is greater than or about equal to the melting point of the gel.

Waxes spanning a range of melt points are commercially available. For example Moore & Munger, Inc. (Shelton, Conn. www.mooremunger.com) sells paraffin waxes with melt points (as measured by ASTM D87, ° F.) of 126, 131, 136, 141, 142, 151, 156, 157 and 159. The wax may be a microcrystalline wax, where Moore & Munger, Inc. sells microcrystalline waxes with melt points (ASMT D87, ° F.) of 130, 156, 161, 165, 170, 175, 176, 178, 179, 181, 186, 188, 195 and 196. The wax may be a synthetic wax produced by the Fischer-Tropsch process. Moore & Munger, Inc. sells synthetic waxes having softening points (Ring & Ball, ° F.) ranging from 203–212. Other vendors of suitable waxes include, for example, Hase Petroleum Wax Company (Arlington Heights, Ill. www.hpwax.com), and the International Group, Inc. (Wayne, Pa. www.igwax.com).

A candle containing a wick, a fuel and a cured coating according to the present invention may optionally contain multiple phases of material. For example, in one embodiment the candle fuel is made up of two different gel phases.

Various decorative items, also referred to as icons, may be placed within the candle fuel. Icons include so-called botanicals, which manufacturers currently place just below the surface of a candle, in order that the shadow of a leaf or otherwise naturally-shaped article can be seen on the candle's surface. Because the candles of the present invention may be transparent, such botanicals may be placed anywhere within the candle, to provide for a pleasing appearance. As another example, colored paraffin beads, or otherwise shaped items, may be added to the molten mixture at an appropriate time during its cooling, so that the decorative items are suspended in the gel. As yet another example, colorant may be gently stirred into the otherwise clear, cooling molten mixture, so that coloration in a swirling pattern may be seen in the final gel.

In one aspect, the present invention provides a solventless, sprayable coating for pillar candles which cures rapidly to a glossy, hard, tack-free film. A preferred method of curing the coating composition on a candle surface involves irradiation with ultraviolet (UV) light in the presence of a photo initiator/sensitizer. Photoinitiators and sensitizers are well known in the art and include without limitation acetophenones, propiophenone, benzophenone, xanthone, fluorenone, benzaldehyde, fluorine, anthriquinone, tripheylamine, and carbazole. A number of photosensitizers and initiators are listed in U.S. Pat. No. 6,172,129. A preferred photosensitizer is IRGACURE® 500 (Ciba, Tarrytown, N.Y.). This curing technique is advantageous because the coating cures in 1–2 seconds when using "H" lamps supplied by Fusion UV Systems, Inc. (Gaithersburg, Md.), thus eliminating packaging delays. This method of coating the candle also results in less labor because the coating can be applied by spraying.

As explained above, in one aspect of the invention, the prepolymer composition can be made by reacting a triacrylate with a primary amine. The resulting prepolymer composition can be cured by UV light when placed on a candle made of a wick and a fuel. In still another aspect of the invention, the triacrylate of the prepolymer composition may be the esterification product of a triol and acrylic acid, and the primary amine of the prepolymer composition may be a primary $C_{14}$–$C_{22}$ hydrocarbon amine. This prepolymer composition may be used to form a candle made of a wick, a fuel, and a cured coating.

In an additional aspect of the invention, the esterification product of a triol and acrylic acid may be trimethylolpropane triacrylate. The primary $C_{14}$–$C_{22}$ hydrocarbon amine of this aspect may be oleyl amine. Hence, trimethylolpropane triacrylate may be reacted with oleyl amine to form the prepolymer curable when applied to a candle made of a wick and fuel.

In a preferred embodiment, a candle is made of a wick, a fuel, and a cured coating. The cured coating may be made from a prepolymer and a leveling agent or flow modifier. A preferred leveling agent is MODAFLOW® 2100 Resin (Solutia Inc., St. Louis, Mo.). The flow modifier may be mixed with the prepolymer composition prior to applying the prepolymer to the candle fuel surface.

The candle of the present invention may be made of a wick, a fuel and a cured coating where the coating also includes one or more additives. The additive in the coating composition may include colorant, fragrance, flame retardant, and insect repellant, for example.

The colorant may, for example, be a pigment or a dye, however a dye is preferred for providing transparent articles. Dyes that are oil soluble are particularly well suited. Oil soluble dyes are well known in the art, and may be obtained from, for example, Pylam Products, Tempe Ariz. Pylam Products sells the following oil soluble dyes: D&C violet #2, D&C yellow #11, D&C green #6, D&C red #17, Pylakrome™ Red, Pylakrome™ brilliant blue, Pyla-Wax™ brilliant blue, Pyla-Wax™ canary yellow, Pyla-Wax™ violet A, and Pyla-Wax™ brilliant red, among others.

The amount of dye which should be present in the coating will depend on the intensity of the dye and the desired strength of the coloration of the candle. This amount can be readily determined by the skilled artisan, with little or no experimentation. Typically, a colorant amount of less than 1 wt. % (based on the total weight of the prepolymer) is satisfactory, and often an amount of less than 0.5 wt. % or less than 0.25 wt. % is satisfactory. The colorant may be mixed together with the coating at any time prior to curing of the prepolymer.

Another optional ingredient is a fragrance. The term "fragrance" is intended to refer to a chemical or blend of chemicals that together have a desirable odor. Fragrances, therefore, typically consist of a blend of chemicals, fragrant chemicals or fragrance materials. A large number of fragrance materials are known and used in various products such as perfumes, cosmetics, soaps, detergents, etc. Any of the fragrance materials used in these products may be added to the prepolymer of the present invention. Bush Boake Allen of Montvale, N.J. sells a large number of fragrance raw materials. Many of these fragrance materials are disclosed in U.S. Pat. No. 6,111,055 and are well known in the art. These fragrance raw materials may be combined in numerous ways to create pleasing fragrances for candles and other compositions disclosed herein.

The amount of fragrance which should be present in the candle will depend on the intensity of the fragrance and the degree to which it is desired that the coating emit fragrance. This amount can be readily determined by the skilled artisan, with little or no experimentation. An amount of fragrance equal to at least about 0.1 wt. %, based on the total weight of the prepolymer, is typically necessary in order to achieve at least some fragrance-emitting character for the composition. Typically, a fragrance amount of less than 50 wt. % (based on the total weight of the prepolymer) is satisfactory, and often an amount of less than 20 wt. % or even less than 15 wt. % is satisfactory. In a typical candle having fragrance, the fragrance constitutes 1–5 wt. % of the total weight of the candle. The amount of fragrance in a candle may depend upon the presence of other optional ingredients. For example, when insect repellent is present in the candle, the fragrance concentration is typically less than 30 wt. % of the total weight of the candle, and preferably is 1–5 wt. %.

The fragrance may be mixed together with the prepolymer after the polyacrylate and primary amine have reacted but before the prepolymer has been cured. It is preferred to add the fragrance to the prepolymer before spraying.

Another optional ingredient is an insect repellent. Suitable insect repellents include, without limitation, citronella, DEET, terpineol, and benzalacetone. In a typical candle, the insect repellent constitutes about 0.1–20 wt. %, preferably 5–10 wt. % of the total weight of the candle.

Still another ingredient may be a flamer retardant. A flame retardant in a coating may be used as a safety feature for a candle. Several flame retardants known in the art may be included in the candle. Suitable flame retardants include, without limitation POLYLITE® 33441-00 (Reichhold, Newark, N.J.), Dyneon™ THV (Dyneon LLC, Oakdale, Minn.), and BAYBLEND® (Bayer Corporation, Pittsburgh, Pa.).

Another aspect of the present invention is a method for coating a candle using a curable composition. The method involves reacting a primary amine with an acrylate selected from the group diacrylate, triacrylate, and tetracrylate, preferably triacrylate, so as to form a product. The product, when intended for UV curing, will include a photoinitiator. The product is then applied to a surface of the candle to provide a curable coating on the candle. The coating is cured with radiation, preferably UV radiation, to provide a cured coating on the candle. The curing conditions should not be too harsh, or else the candle may be damaged. For this reason, electron beam is not a preferred energy source for curing the coating. Even too much UV radiation can damage the candle, particularly when the candle is formed from a gel.

The method of applying the coating may be performed in a variety of ways. These application techniques include spraying, brushing, dipping, and sponging. In a preferred technique, the candle is coated by spraying the prepolymer onto the candle surface followed by curing by exposure to radiation, particularly UV radiation. When the prepolymer composition viscosity is rather high at room temperature, the coating composition may be heated before it is applied to a candle surface. In the alternative, those skilled in the art would appreciate suitable diluents that may be added to the composition to affect the prepolymer's viscosity.

The coating thus preferably directly contacts the exterior surface of the underlying candle and at least partially encases that candle. Where the candle has a top, a bottom and one or more sides, the coating preferably covers all of the sides of the candle, and optionally the top and bottom. The coating preferably covers all of the sides of the candle because this is the area of the candle which is primarily seen by the consumer. In an alternative embodiment, the coating may also cover the sides and the bottom of the candle to inhibit or prevent discharge of the candle fuel when the candle fuel is nearly consumed.

The coating should conform to the exterior surface of the candle, in that the coating is in direct contact with all of the surface which is covered by the coating. If the candle has a patterned exterior surface, e.g., relief images or a ribbed texture, then the coating either follows the exact contours of the pattern so that the exterior surface of the coating likewise contains that (or perhaps a different) pattern, or that portion of the coating which directly contacts the candle will be conformal in exactly following the contours of the candle's surface but the exterior surface of the coating is smooth and without pattern. Where the exterior surface of the coating is smooth but the exterior surface of the candle has a relief image, the coating should be transparent so that the underlying relief image can be viewed through the coating.

In another aspect of the invention, the prepolymer coating may be applied to a candle surface that already contains a coating. Thus, a method for applying a coating to a candle may include reacting a primary amine with an acrylate selected from the group diacrylate, triacrylate, and tetraacrylate to form a product. That product may be applied to a surface of a candle to provide a curable coating on a candle. Curing of the coating with irradiation provides the first coated surface of the candle. An additional coating may be applied by repeating these steps.

The method for coating a candle may be modified to include additional ingredients in the curable composition. In one aspect of the invention, a primary amine is reacted with an acrylate selected from the group diacrylate, triacrylate, and tetraacrylate to form a product. A photosensitizer or initiator is added to this product. The product is then applied to a surface of the candle to provide a coating on the candle. The coating is cured with radiation to provide a cured coating. In another aspect of the invention, a leveling agent may be included in the curable composition. In still another aspect of the invention, an additive selected from colorant, fragrance, flame retardant and insect repellant may be included in the curable composition.

In another aspect of the invention, a further method for coating a candle is provided. In this method a primary amine, preferably a $C_{14}$–$C_{22}$ primary amine, and a triacrylate, preferably TMPTA, are reacted to give a product. The product is applied to a surface of a candle to provide a curable coating on the candle. The coating is cured with irradiation, preferably UV radiation.

The following Examples are set forth as a means of illustrating the present invention and are not to be construed as a limitation thereon. In the following Examples a 250 ml 3-neck flask was equipped with an agitator, nitrogen inlet, thermometer with thermowatch, equilibrium addition funnel, and heating mantle. A Minolta Chroma Meter 310 was used to obtain the equivalent Gardner color. Cross Hatch Adhesion was determined on a scale of 0–5 (5 being the best) according to ASTM D-3359. Pencil Hardness was determined on a scale of 6B–9H (9H being the hardest) according to ASTM D-3363. Impact Resistance (a measure of flexibility) was determined in in-lbs. with a Model #172 Universal Impact Tester according to ASTM D-2794.

EXAMPLES

Example 1

A 250 mL reaction flask was charged with 100.0 g of AGEFLEX® TMPTA (trimethylolpropane triacrylate, Ciba Specialty Chemicals) and stirred at room temperature and provided with a nitrogen sweep. This was followed by the dropwise addition of 33.83 g of Kemamine® 989D (oleyl amine, Witco). The reaction mixture was allowed to exotherm. The reaction mixture was then heated to 60° C. and held at that temperature for 4.5 hours. Stirring and nitrogen sweep were discontinued followed by the addition of 0.067 g of HQMME (hydroquinone monomethyl ether, Eastman). After the HQMME was observed to melt, the reaction mixture was stirred for 30 minutes. The product was cooled, discharged from the flask, and characterized as follows: Gardner color—1.2; Brookfield viscosity—630 centipoise (cps) at 25° C. and 99 cps at 55° C. After 7 days at room temperature the viscosity was found to be stable (890 cps at 25° C. and 126 cps at 55° C.) A free TMPTA content of 25.4% was determined by GPC (gel permeation chromatography) of the stable product.

To determine the cured film properties of the final product (having a viscosity of 630 cps at 25° C.), 10.0 g of the product was mixed with 0.3 g of IRGACURE® 500 photoinitiator (Ciba) and 0.1 g of Modaflow™ 2100 Resin. A 1.5 mil (1.5 thousands of an inch) wet thickness film was drawn down on a cold rolled steel panel using an 8-pass wet film applicator. The coated substrate was suspended in a Rayonet UV reactor (16×3000Å"A" type lamps) for 4 minutes. The resulting cured coating had a smooth glossy surface with the following properties: Cross Hatch Adhesion—5; Pencil Hardness—8H; and Impact Resistance of Pass 100 Forward and Pass 40 Reverse.

Example 2

A 2 L reaction flask was charged with 613.4 g of AGEFLEX™ TMPTA and stirred at room temperature and provided with a light nitrogen sweep. KENAMINE™ 989D (276.7 g, Witco Chemicals) was added dropwise. The reaction mixture was allowed to exotherm, then heated to 60° C.

and held at that temperature for 4.5 hours. The agitator and nitrogen flow were turned off, followed by addition of 0.45 g of HQMME. After the HQMME was observed to melt, the reaction mixture was stirred for 30 minutes. The product was cooled, discharged from the flask, and characterized as follows. Gardner equivalent color, as measured with the Minolta Chroma Meter 310 was −0.6; Brookfield viscosity was 930 cps at 25° C. and 185 cps at 55° C. After 7 days at room temperature, the viscosity of the product was found to be stable (1,770 cps at 25° C. and 241 cps at 55° C.) A free TMPTA content of 16.0% was determined by GPC of the stable product.

To determine the cured film properties of the final product, 10.0 g of the product was mixed with 0.3 g of IRGACURE® 500 photoinitiator and 0.1 g of Modaflow™ 2100 Resin. A 1.5 mil wet thickness film was drawn down on a cold rolled steel panel using an 8-pass wet film applicator. The coated substrate was suspended in a Rayonet UV Reactor (16×3000 Å "A" type lamps) for 4 minutes. The resulting cured coating had a smooth glossy surface with the following properties: Cross Hatch Adheison—5; Pencil Hardness—7H; and Impact Resistance of Pass 90 Forward and Pass Reverse 40.

Example 3

A 500 mL reaction flask was charged with 200.0 g of AGEFLEX® TMPTA and stirred at room temperature and provided with a light nitrogen sweep. Kenamine® 989D (67.7 g) was added dropwise. The mixture was allowed to exotherm followed by heating to 60° C. and held at that temperature for 4.5 hours. Stirring and nitrogen sweep were discontinued followed by addtion of 0.134 g of HQMME. After the HQMME was observed to melt, the reaction mixture was stirred with light nitrogen sweep and heated to 60° C. and held to that temperature for 11.5 hours. The product was cooled, discharged, and characterized as follows: Brookfield viscosity—121 cps at 55° C.

Example 4

Initial attempts at coating an oily substrate (candle) with the prepolymer of Example 2 involved applying the coating with a sponge brush. However, flow problems were observed due to incompatibility between the coating and the oily surface of the candle. This caused the coating to bead and streak. A sample of MODAFLOW® 2100 Resin, which is a flow modifier from Solutia, was added to the coating blend at a 1.0 wt% level, based on the total weight of the coating. The addition of the flow modifier resulted in an even coating on the oily surface without beading or streaking.

Since spraying the coating would be the preferred method in a commercial setting, an automotive touch up sprayer (aspiration type), an air compressor, and related accessories were obtained. It was determined, based on Brookfield viscosity, that a material such as Example 1 could be effectively sprayed at 50–55° C. and a material such as Example 2 could be effectively sprayed at 55–60° C. The spraying temperature was maintained using a small electric heating mantle equipped with a voltage regulator. The exposed portion of the sprayer was warmed, as required, with a heating gun to allow free flow through the nozzle. The optimum pressure was found to be less than or equal to 10 psi. This pressure provided a suitable amount of spray without air entrapment in the form of bubbles.

Coating thickness was found to be very important. A coating that was too thin would be diluted by oil absorbed from the surface of the candle and would not cure properly. A coating applied too thickly would result in an irregular surface due to overflow of the excess. The optimum thickness was obtained through experience and subjective observation, but does not require undue experimentation, as trying just a couple different thicknesses in the range of 1–10 mils gave a good idea of a suitable thickness. Based on the measured weight of coating applied and known surface area of the candle, it was calculated that a suitable coating was 7–8 mils thick.

A preferred coating formulation is 100 parts of the prepolymer from Example 2, 3 parts IRGACURE™ 500 photoinitiator and 1 part MODAFLOW® 2100 Resin. The candle was suspended by its wick from an electric stirring motor and rotated during spray application. When a sufficient amount of the coating formulation was applied, the candle was suspended by its wick in a Rayonet UV Reactor (16×3000A "A" type lamps) for 3 to 4 minutes. The resulting cured coating was clear, glossy, hard, and smooth to the touch.

All publications and patent applications mentioned in this specification are herein incorporated by reference to the same extent as if each individual publication or patent application was specifically and individually incorporated by reference. For instance, the present application fully incorporates by reference all disclosure from co-pending U.S. patent application Ser. No. 09/292,486 filed Apr. 15, 1999, now allowed, which is both a continuation of PCT/US97/18821 having an International Filing Date of Oct. 18, 1997, and a continuation-in-part of U.S. patent application No. 08/939,034, filed Sep. 26, 1997, now U.S. Pat. No. 6,111,055 issued Aug. 29, 2000. The present application also fully incorporates by reference all disclosure contained in parent application U.S. patent application Ser. No. 08/939,034, filed Sep. 26, 1997, now U.S. Pat. No. 6,111,055.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A candle comprising a wick, a fuel, and a cured coating.

2. The candle of claim 1 wherein the fuel comprises a gellant.

3. The candle of claim 2 wherein the gellant is an ETPA resin of the formula

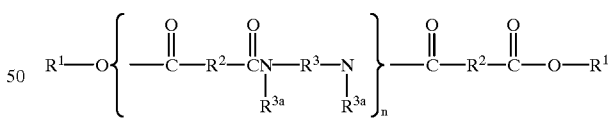

wherein n designates a number of repeating units such that ester groups constitute from 10% to 50% of the total of the ester and amide groups; $R^1$ at each occurrence is independently selected from an alkyl or alkenyl group containing at least 4 carbon atoms; $R^2$ at each occurrence is independently selected from a $C_{4-42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

4. The candle of claim 2 wherein the gellant is an ATPA resin of the formula

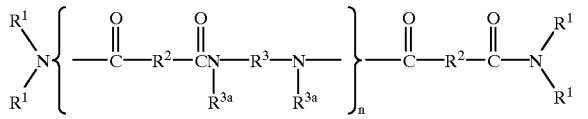

wherein, n designates a number of repeating units such that terminal amide groups constitute from 10% to 50% of the total amide groups; $R^1$ at each occurrence is independently selected from a $C_{1-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$.

5. The candle of claim 1 wherein the fuel comprises mineral oil or triglyceride.

6. The candle of claim 1 wherein the candle comprises more than one visible phase.

7. The candle of claim 1 wherein the candle comprises an icon.

8. The candle of claim 1 wherein the coating is a UV cured coating.

9. The candle of claim 8 wherein the UV-cured coating is a reaction product of a triacrylate and a primary amine.

10. The candle of claim 9 wherein triacrylate is the esterification product of a triol and acrylic acid, and the primary amine is a $C_{14}$–$C_{22}$ fatty amine.

11. The candle of claim 10 wherein the triacrylate comprises trimethylolpropane triacrylate and the primary amine comprises oleyl amine.

12. The candle of claim 1 wherein the coating comprises a leveling agent.

13. The candle of claim 1 wherein the coating comprises an additive selected from colorant, fragrance, flame retardant and insect repellant.

14. A method for coating a candle using a curable composition comprising
(a) reacting a primary amine with a triacrylate to form a product;
(b) applying the product to a surface of a candle to provide a curable coating on said candle; and
(c) curing the curable coating with radiation, to provide a cured coating on said candle.

15. The method of claim 14 wherein applying the product is performed by spraying, brushing, dipping, or sponging.

16. The method of claim 14 wherein applying the product is performed by spraying.

17. The method of claim 14 further comprising applying one or more additional layers of coating, to provide a multiply-coated candle.

18. The method of claim 14 wherein the product further comprises a photosensitizer or a photoinitiator.

19. The method of claim 14 wherein the product further comprises a leveling agent or a flow modifier.

20. The method of claim 19 wherein the flow modifier is a copolymer of ethyl acrylate and 2-ethylhexyl acrylate, said copolymer having a viscosity at 25° C. of 5,000 to 12,000 centipoise.

21. The method of claim 14 wherein the product comprises an additive selected from colorant, fragrance, flame retardant and insect repellant.

22. The method of claim 14 wherein the product is a reaction product of a triacrylate and a $C_{14}$–$C_{22}$ primary fatty amine.

23. The method of claim 14 wherein the product is a reaction product of trimethylolpropane triacrylate and oleyl amine.

24. A method for coating a candle using a curable composition comprising
(a) reacting a $C_{14}$–$C_{22}$ primary fatty amine with a triacrylate to form a product, the product further comprising a photoinitiator and a leveling agent;
(b) applying the product to a surface of a candle to provide a curable coating on said candle; and
(c) curing the curable coating with radiation, to provide a cured coating on said candle.

25. The method of claim 24 wherein the leveling agent is a copolymer of ethyl acrylate and 2-ethylhexyl acrylate, said copolymer having a viscosity at 25° C. of 5,000 to 12,000 centipoise.

26. A candle comprising a wick, a fuel, and a cured coating, where the cured coating is the reaction product of UV-curing a coating composition, the coating composition comprising a reaction product of a primary $C_{14}$–$C_{22}$ fatty amine with a poly(meth)acrylate, a leveling agent and a photoinitiator.

27. The candle of claim 26 wherein the primary amine is oleyl amine and the poly(meth)acrylate is trimethylolpropane triacrylate.

28. The candle of claim 26 wherein the fuel comprises solvent and gellant for the solvent.

29. The candle of claim 26 wherein the leveling agent is a copolymer of ethyl acrylate and 2-ethylhexyl acrylate, said copolymer having a viscosity at 25° C. of 5,000 to 12,000 centipoise.

* * * * *